United States Patent [19]

Chiovini et al.

[11] 4,407,834
[45] Oct. 4, 1983

[54] RECOVERY OF XANTHINE STIMULANTS FROM AQUEOUS MEDIA

[75] Inventors: Jacky Chiovini, Daillens; Geoffrey Margolis, Bussigny; Maurice Blanc, Morges, all of Switzerland

[73] Assignee: Societe d'Assistance Technique pour Produits Nestle S.A., Lausanne, Switzerland

[21] Appl. No.: 286,632

[22] Filed: Jul. 24, 1981

Related U.S. Application Data

[63] Continuation-in-part of Ser. No. 266,091, May 21, 1981, Pat. No. 4,390,698.

[51] Int. Cl.³ ............................................... A23G 1/00
[52] U.S. Cl. ..................................... 426/422; 426/427
[58] Field of Search ................................ 426/422, 427

[56] References Cited

U.S. PATENT DOCUMENTS 4,160,042  7/1979  Farr et al. ........................... 426/422

OTHER PUBLICATIONS

Minifie, Chocolate, Cocoa, and Confectionery: Science & Technology, 2nd Ed., 1980, Avi: Westport, Conn., p. 346.
Hassler, Active Carbon, 1951, Chemical Publ. Co., Inc., New York, pp. 21, 184, 358–360.
Hassler, Purification with Active Carbon–Industrial, Commercial, Environmental, Chemical Publ. Co.: New York, pp. 34, 37, 91, 182–183, 346–348.

Primary Examiner—Joseph M. Golian
Attorney, Agent, or Firm—Vogt & O'Donnell

[57] ABSTRACT

A process for the recovery of xanthine stimulants from an aqueous solution containing xanthine stimulants extracted from cocoa material, which comprises contacting the solution with a substantially neutral adsorbent and separating the adsorbent, with the xanthine stimulants adsorbed thereon, from the aqueous solution having a reduced content of xanthine stimulants.

7 Claims, No Drawings

RECOVERY OF XANTHINE STIMULANTS FROM AQUEOUS MEDIA

This is a continuation-in-part of application Ser. No. 266,091, filed May 21, 1981 and now U.S. Pat. No. 4,390,698.

The present invention is concerned with the recovery of xanthine stimulants from aqueous media.

The preparation of soluble cocoa by the extraction of cocoa material with water is well-known. During the extraction process certain methyl-substituted xanthines such as theobromine and caffeine are extracted along with other water-soluble solid materials. However, it is often desirable to prepare a soluble cocoa substantially free from such stimulating substances, which are referred to in this invention as xanthine stimulants, and these may be removed from the extract by adsorption on a solid adsorbent after which the extract substantially free of xanthine stimulants is returned to the cocoa material. Various solid adsorbents have been suggested, such as polymeric resins and activated carbon, but they can cause a deterioration in the colour of the cocoa material. For example, if activated carbon is used, the contact between the aqueous extract and activated carbon often leads to an increase in pH which is associated with the deterioration in the colour of the cocoa material.

We have now found that this undesirable deterioration in colour may be considerably diminished if the adsorbent used shows a substantially neutral reaction on dispersion in water.

According to the present invention there is provided a process for the recovery of xanthine stimulants from an aqueous solution containing xanthine stimulants extracted from cocoa material, which comprises contacting the solution with a substantially neutral adsorbent and separating the adsorbent with the xanthine stimulants adsorbed thereon, from the aqueous solution having a reduced content of xanthine stimulants. The term "substantially neutral" used to describe the adsorbent means that when the adsorbent is immersed in water the pH value is substantially unchanged. An example of a resin adsorbent having this property is semi-calcinated resin XE-340 manufactured by Rohm & Haas. However it is preferred to use activated carbon having this property which may be obtained either by acid washing of thermally activated carbon followed by rinsing with water to neutrality, or by neutralisation of acid-activated carbon with an aqueous alkali followed by rinsing with water to neutrality. The term "reduced content" in the present context is intended to cover zero content.

The aqueous solution containing the xanthine stimulants may by extracted from cocoa material by conventional methods, involving contact of the cocoa material with an aqueous medium which may be water, preferably deionised water, an aqueous solution of cocoa solids free of xanthine stimulants, or an aqueous solution of cocoa solids containing a minor amount of xanthine stimulants, for a period of time sufficient to reduce the content of xanthine stimulants in the cocoa material to the desired level. The cocoa material may be any cocoa-containing mass, for example green cocoa beans, roasted cocoa beans or roasted cocoa nibs, but is preferably the green, ground, unroasted cocoa nibs formed by cleaning, cracking and winnowing the cocoa beans to remove filth, germs and most of the shell material, followed by grinding. The extraction may be carried out batchwise or in a continuous counter-current extraction system containing a plurality of columns.

The ratio of water to the cocoa material during the extraction is not critical but is in general determined having regard to practical considerations imposed by industrial operations. Excessive volumes of water should be avoided, as also water to cocoa ratios which do not provide for adequate extraction of the xanthine stimulants. Conveniently, a weight ratio of water to cocoa material from 5 to 200 parts and preferably from 10 to 100 parts of water per part of cocoa material gives satisfactory results.

In a batchwise extraction process, a fixed weight of the cocoa material is contacted as a static bed, in a column, or in a suitable tumbler or like extractor with a fixed volume of water. The water is continuously recycled whereby water containing the xanthine stimulants is withdrawn from the column or extractor and the xanthine stimulants removed by contacting a neutral adsorbent contained in another column, prior to its return to the cocoa material. The total contact time will depend, inter alia on the water/cocoa ratio, the temperature, and the degree of removal of the xanthine stimulants that is desired and is usually from 1 to 10 hours, preferably from 2 to 3 hours. The temperature may be, for example, from 40° to 100° C., preferably from 70° to 95° C. at atmospheric pressure, or higher if the extraction takes place under pressure.

In a continuous counter-current extraction process, water passes through an extraction system comprising a plurality of cells containing the cocoa material whereby the water enters the extraction system at a cell containing the most exhausted batch of cocoa material, passes through progressively fresher batches of cocoa material contained in successive cells and is finally drawn off from the cell containing the freshest batch of cocoa material. The temperature of the water entering the cell containing the most exhausted cocoa material may be from 40° to 100° C. preferably from 70° to 95° C. at atmospheric pressure, or higher if the extraction takes place under pressure. The number of cells and cycle time are chosen to give the desired extraction of xanthine stimulants. Up to eight cells, in series, may be used with a cycle time of from 15 to 120 minutes.

The aqueous extract containing the xanthine stimulants and other solids may be concentrated before the xanthine stimulants are removed by contacting with the neutral adsorbent, for example in a counter-current system. In such a system the adsorbent is contained in several columns and the extract passes through these columns in series. Periodically the most saturated column is removed from the system and one containing fresh adsorbent added. The temperature in the columns is conveniently above 40° C. and preferably from 70° to 95° C. The number of columns, the cycle time for each column and the residence time of the extract are chosen to achieve the degree of removal of the xanthine stimulants that is desired and to minimise the quantity of adsorbent used. The weight of adsorbent is usually from 10 to 20% of the weight of cocoa material from which the xanthine stimulants are being extracted. If desired, the content of the xanthine stimulants in the aqueous solution may be reduced substantially to zero by the process.

During contact of the aqueous extract with the neutral adsorbent a proportion of the other solids are adsorbed in addition to the xanthine stimulants. Part of these adsorbed solids, for example, 70 to 80%, can be recuperated without desorbing the xanthine stimulants by washing the adsorbent, for example with water.

Whether the adsorbent is used in the batch or the counter-current continuous system, provision is advantageously made for continuity of operation by duplicating the beds of adsorbent so that one or more may be renewed whilst the others are on stream.

After the removal of the xanthine stimulants is terminated, it is usually desirable, to avoid excessive losses, to reincorporate the other solids present in the aqueous extract into the cocoa material having a reduced content of xanthine stimulants.

Various techniques may be used. For example, the cocoa material may be pre-dried, at a temperature below 100° C., preferably from 60° to 70° C., preferably to a moisture content of from 2 to 7.5% and combined directly with the extract. Alternatively, the extract may be pre-concentrated, for example, by evaporation, to a solids content of from 5% to 25% before contact with the cocoa material. Preferably both the cocoa material and the extract are treated in this way, that is, the cocoa material is pre-dried and the extract pre-concentrated before the reincorporation.

Satisfactory reincorporation of the solids may be obtained after 2 hours, preferably from 5 to 8 hours, at a temperature above 40° C. and preferably from 60° to 80° C. Desirably, the total amount of water present is such that the final moisture content of the cocoa material is from 30 to 60%, preferably from 50 to 55%.

The cocoa material containing the reincorporated solids is then dried to a moisture content of 2 to 5% by weight before being roasted. The roasted material may be used in the normal way for the production of cocoa drinks or chocolate.

In a modification, the amount of solids other than xanthine stimulants contacted with the cocoa material may be less than the amount extracted along with the xanthine stimulants.

Periodically, the adsorbent may be regenerated, usually by heating or solvent extraction. If desired, the xanthine stimulants may be recovered from the adsorbent by solvent extraction, for example, with an aliphatic alcohol such as ethanol or a chlorinated hydrocarbon, such as methylene dichloride.

The following Examples further illustrate the present invention. Parts and percentages are expressed by weight unless otherwise stated.

EXAMPLE 1

Neutralised activated carbon was prepared by washing commercial thermally activated carbon with 2% hydrochloric acid followed by rinsing with deionised water (pH=6) until the pH of the washings is constant at 6.0.

100 parts of green, ground unroasted cocoa nibs were contacted at 80° C. in a column with 1'100 parts of water. Clearbrown water containing xanthine stimulants was continuously withdrawn from the column and the xanthine stimulants removed by contacting neutral activated carbon contained in another column and recycled to the cocoa nibs. After two hours the brown aqueous extract was concentrated by evaporation to 90 parts. The exhausted cocoa nibs were dried at 65° C. for 18 hours until the moisture content was reduced to 5%. The concentrated aqueous extract was reincorporated into the dried cocoa nibs in a mixer at 70° C. for 6 hours to give a cocoa material containing 53% moisture. The cocoa material having all the soluble materials reincorporated therein was dried at 70° C. for 12 hours and then roasted. The amount of theobromine in the cocoa was reduced from 1.30% to 0.04%, that is a 97% reduction. Whereas the colour of the extract substantially free of xanthine stimulants showed only a slight difference from the extract containing xanthine stimulants, the colour of an extract, from which the xanthine stimulants had been removed by contacting unwashed carbon, was greyish-black.

EXAMPLES 2 TO 6

A similar procedure to that described in Example 1 was followed except that the time of contact, the temperature, the water: cocoa ratio, the loss of solid materials other than xanthine stimulants and the degree of detheobromination (DTB) achieved are given in the following Table.

TABLE I

| Example | Time of contact (hours) | Temp. (°C.) | Water: Cocoa ratio | Loss of solid materials | DTB % |
|---|---|---|---|---|---|
| 2 | 2 | 60 | 10 | 9.4 | 64 |
| 3 | 2 | 80 | 10 | 11.0 | 76 |
| 4 | 2 | 95 | 10 | 11.0 | 82 |
| 5 | 2 | 95 | 20 | 11.6 | 92 |
| 6 | 3 | 80 | 100 | 17.4 | 98 |

EXAMPLE 7

A similar procedure to Example 3 was followed but in which the water was forced to flow from the bottom to the top of the column containing the cocoa nibs. The loss of solid materials was 10.5% while the amount of detheobromination was 90.4%.

EXAMPLE 8

Green, ground, unroasted cocoa nibs were formed by cleaning, cracking and winnowing the cocoa beans to remove filth, germs and most of the shell material, followed by grinding. Xanthine stimulants were extracted from these green, ground, unroasted cocoa nibs continuously by counter-current extraction with an aqueous solution. 4 extractors in series were used, each containing 200 parts of the cocoa nibs. The extraction was carried out with deionised water at 80° C. entering the most exhausted extractor. A clear brown aqueous solution containing xanthine stimulants and other solids was removed at 80° C. from the extractor containing the least exhausted cocoa, the cycle time being 30 minutes. The last extractor containing cocoa from which xanthine stimulants have been extracted was removed from the system and one containing fresh green, ground, unroasted cocoa nibs was added once every two hours. The ratio of water to cocoa nibs was 10:1 so that the flow rate of water through the cystem was 4000 parts/hr and the aqueous solution removed contained 1% dissolved solids.

The extract coming from the least exhausted cocoa was passed countercurrently through 2 columns in series, each column containing 50 parts of neutralised, activated carbon prepared in a manner similar to that described in Example 1. The temperature in the columns was maintained at 80° C. The most saturated carbon column was removed and a fresh one added every 4 hours. The saturated carbon columns were washed with water flowing at 4000 parts/hr and the brown aqueous solution removed contained 0.7% dissolved solids other than xanthine stimulants.

The cocoa nibs from which xanthine stimulants have been extracted were dried to a moisture content of 5% and mixed with the corresponding extract from which xanthine stimulants have been removed, which extract contains dissolved solids other than xanthine stimulants and which has first been concentrated by evaporation to contain 7% solids. Thereafter, the cocoa nibs containing 50% moisture were dried to 5% moisture content. The degree of detheobromination was 97%.

EXAMPLE 9

A similar procedure to that described in Example 1 was followed except that the clear brown water containing xanthine stimulants was contacted with semi-calcinated resin XE-340 manufactured by Rohm & Haas to remove the xanthine stimulants. The colour of the extract substantially free of xanthine stimulants was also clear brown showing no difference from the water containing xanthine stimulants.

EXAMPLE 10

By following an identical procedure to that described in Example 1 but using cocoa nibs containing 1.399% theobromine instead of 1.30%, the content of theobromine was reduced to 0.042%, that is a 97% reduction. In this Example, the caffeine content was also measured and it was found to have been reduced by the process from 0.070% to 0.002%, also a 97% reduction.

We claim:

1. A process for the recovery of xanthine stimulants from an aqueous solution containing xanthine stimulants extracted from cocoa material, characterised in that the solution is contacted with a substantially neutral adsorbent and the adsorbent with the xanthine stimulants adsorbed thereon is separated from the aqueous solution having a reduced content of xanthine stimulants.

2. A process according to claim 1, wherein the cocoa material is the green, ground, unroasted cocoa nibs formed by cleaning, cracking and winnowing the cocoa beans to remove filth, germs and most of the shell material, followed by grinding.

3. A process according to claim 1 or claim 2, wherein the contacting is effected at a temperature of from 70° to 95° C.

4. A process according to claim 1, wherein the content of the xanthine stimulants in the aqueous solution is reduced substantially to zero and the other solids therein are combined with the cocoa material having a reduced content of xanthine stimulants and other water-soluble solid materials.

5. A process for the removal of xanthine stimulants from cocoa material characterised in that the cocoa material is contacted with an aqueous medium, the aqueous medium containing xanthine stimulants dissolved from the cocoa material is recovered, xanthine stimulants are removed from this medium by contact with a substantially neutral adsorbent, the adsorbent with xanthine stimulants adsorbed thereon is separated from the aqueous medium having a reduced content of xanthine stimulants and the other solids present in the aqueous medium having a reduced content of xanthine stimulants is combined with cocoa material having a reduced content of xanthine stimulants and of other solids.

6. A process according to claim 5, wherein the content of xanthine stimulants in the aqueous medium is reduced substantially to zero.

7. A process according to claim 1 or claim 5, wherein the adsorbent is substantially neutral activated carbon.

* * * * *